United States Patent [19]

Buchhave et al.

[11] Patent Number: 4,701,051
[45] Date of Patent: Oct. 20, 1987

[54] LASER-DOPPLER-APPARATUS FOR DETERMINING THE SIZE OF MOVING SPHERICAL PARTICLES IN A FLUID FLOW

[75] Inventors: Preben Buchhave, Birkerod; John Knuhtsen, Virum; Peder E. S. Olldag, Humlebaek, all of Denmark

[73] Assignee: Dantec Electronik, Medicinsk Og Videnskabeligt Maleudstyr A/S, Skovlunde, Denmark

[21] Appl. No.: 698,182
[22] PCT Filed: May 18, 1983
[86] PCT No.: PCT/DK83/00054
 § 371 Date: Jan. 16, 1985
 § 102(e) Date: Jan. 16, 1985
[87] PCT Pub. No.: WO84/04592
 PCT Pub. Date: Nov. 22, 1984
[51] Int. Cl.[4] .......................................... G01N 15/02
[52] U.S. Cl. .................................... 356/336; 356/343
[58] Field of Search .................. 356/336, 338; 250/574
[56] References Cited

U.S. PATENT DOCUMENTS 4,179,218 12/1979 Erdmann et al. .................... 250/574
4,540,283 9/1985 Bachalo ............................... 356/336

OTHER PUBLICATIONS

"Measurement of Particle Size, Number Density, and Velocity Using a Laser Interferometer"Farmer, 11/1972, vol. 11, #11, *Applied Optics*.

*Primary Examiner*—R. A. Rosenberger
*Assistant Examiner*—Crystal Cooper
*Attorney, Agent, or Firm*—Larson and Taylor

[57] ABSTRACT

In a laser-doppler-apparatus, the size of moving spherical particles in a fluid flow is determined by crossing two spatially separated laser beams (15, 16) to intersect each other under a given angle ($\theta$) in a measuring volume passed by a part of the fluid flow. By means of two photoelectric measuring detectors (17, 18) arranged in different spatial positions outside the measuring volume, scattered rays from a moving particle are detected in the form of doppler signals having different phase. The particle size is determined by generating a resulting phase difference signal ($\phi_M$) from the signals from the two measuring detectors (17, 18). By combining the signal from one measuring detector (17) with the signal from a reference detector (19) positioned between the two measuring detectors, a phase reference signal ($\phi_R$) is generated to indicate whether the resulting phase difference signal ($\phi_M$) has been caused by a phase difference between the doppler signals exceeding $2\pi$.

7 Claims, 5 Drawing Figures

LASER-DOPPLER-APPARATUS FOR DETERMINING THE SIZE OF MOVING SPHERICAL PARTICLES IN A FLUID FLOW

The invention relates to a laser-doppler-apparatus for determining the size of moving spherical particles in a fluid flow, comprising a laser beam generator for generating two spatially separated laser beams, focusing means for focusing the laser beams so that in a focusing plane, the focused beams intersect each other under a given angle in an intersecting point in a measuring volume passed by a part of the fluid flow, photoelectric detector means for detecting the scattered radiation caused by a moving particle in the fluid flow in spatially different positions outside the measuring volume and generating electrical signals in response thereto, and signal processing means for determining the particle size on the basis of said electrical signals.

In optical measuring methods for determining the size of moving particles in a fluid flow by use, for instance, of laser radiation, the measurement may take place without physical interference with the measuring medium in a small volume of space, the measuring volume, which is passed by the fluid flow or a part thereof and is defined by intersection between two incoming laser beams, on one hand, and by location within the viewing field of an optical detector, on the other hand. Moreover, the measurement may be performed in real time at a high data collection rate and with a possibility of getting simultaneous information about the size and velocity of moving micro elements in the fluid flow.

Such micro elements may have the form of solid particles, droplets in gases or gas bubbles in liquids, and in the following all three kinds are considered to be encompassed by the designation "particles".

The methods hitherto in use for optical determination of particle size have mainly been based on measurement of the intensity of the scattered radiation from a particle passing the measuring volume. However, the spatial function of the scattered radiation from small particles is a complicated function of the direction of the scattered radiation relative to the direction of the incoming radiation, the direction of polarization of the radiation and the size, shape and material of the particle.

In order to reduce this complexity, it has been suggested, inter alia, to measure the intensity of the scattered radiation concurrently in two or more directions or measure the overall intensity within a spatial angle in a direction normal to the incoming light.

Furthermore, measuring methods are known for optical article size measurement which are based on detection of different properties of so-called laser-doppler signals. Thus, for measuring the velocity of particles in a flowing medium, it is well known to measure the doppler shift of the frequency of scattered laser radiation from the moving particle. In general, this principle for measurement of flow velocity is based on measurement of the difference between the doppler shifts of scattered radiation from two different laser beams intersecting each other under a given angle in the measuring volume, the two beams of scattered radiation being caused to impinge simultaneously and in overlapping relationship on the surface of a photo detector. Thereby, the difference frequency between the two doppler-shifted radiation frequencies is formed, and this difference frequency is direcly proportional to the velocity component of the particle normal to the bisector of the two incoming beams in the plane of the incoming beams.

In addition to the information about the velocity of a moving particle associated with the frequency, a doppler signal also comprises information about other properties of the particle, such as its size, and, therefore, different methods have also been suggested for deriving information about the size of moving particles from doppler signals. Thus, a relatively simple prior art method is based on measurement of the amplitude of a low-pass-filtered doppler signal.

From an article of W. M. Farmer, "Measurement of Particle Size, Number Density and Velocity Using a Laser Interferometer", in Applied Optics, Vol. 11, November 1972, pages 2603–2612, the so-called visibility method is known, which is based on utilization of the fact that the depth of modulation of the measured doppler signal will be dependent on the size of the moving particle relative to the distance between parallel interference planes in the intersection region between the incoming beams. In this method, the so-called visibility factor is determined as the ratio of a high-pass-filtered to a low-pass-filtered part of the doppler signal. However, in its original form as described in the above mentioned article, this measuring method was limited to scattered radiation resulting mainly from diffraction in the bisector plane between the two incoming beams.

A later development of this theoretical basis has led to an apparatus known from U.S. Pat. No. 4,329,054 for measuring the scattered radiation from spherical droplets in gases in directions forming an angle with the bisector plane where the scattered radiation is mainly caused by refraction in a droplet or reflection from the surface thereof.

In a further elaboration of this theoretical basis, it has been disclosed in a lecture published by F. Durst and M. Zaré: "Laser Doppler Measurements in Two-Phase Flows", Proceedings of the LDA-Symposium, Copenhagen 1975, pages 403–429, that a doppler signal from a droplet in a gas flow will comprise a phase term depending on the radius of the droplet, as well as the direction to the detector and the aperture thereof.

In a later theoretical and experimental work by Franz Durst: "Review—Combined Measurements of Particle Velocities, Size Distributions, and Concentrations" in Transactions of the ASME, Vol. 104, September 1982, pages 284–296, the properties of laser radiation is described, which is scattered from great bubbles in water or big reflecting bodies in gas. Thereby, it has been demonstrated that by irradiation of such a body with the two laser beams as employed in a usual laser doppler-anemometer, interference stripes are formed in the region around the body due to phase differences between the scattered radiations from the two incoming beams against a common point of observation. Thereby, it has been demonstrated that the phase difference between radiations scattered in the forward or backward direction relative to the bisector or the two incoming beams will contain information about the radius of the spreading spherical body. However, the results found thereby will apply only to relatively big bodies and only for scattered radiation in the forward and backward directions. Moreover, the phase information contains an ambiguity which reduces or completely prevents the possibility for utilizing the results found in measuring instruments for practical purposes.

Whereas the above mentioned hitherto suggested methods have mainly been based on theoretical considerations and scientific experimental verifications thereof and have, moreover, either been based on measurement of the radiation intensity in interference patterns or have been limited for the last-mentioned true laser doppler method to measurement of relatively great particles and have suffered from an ambiguity in the size information, it is the object of the invention to provide a design af a laser-doppler-apparatus suitable for practical measuring instruments, whereby an unambiguous information can be obtained about the size of moving particles in a fluid flow within a controllable variation range of particle sizes for particle dimensions quite down to an order of size corresponding to the wave length for the laser radiation.

According to the invention, a laser-doppler-apparatus of the kind mentioned hereinbefore is characterized in that the detector means comprise two measuring detectors and means for adjusting the detectors into spatial positions, for which in a detecting plane the beam directions from said intersecting point to the measuring detectors have an angular separation corresponding to a predetermined maximum particle size, for receiving scattered beams from the moving particle in the form of doppler signals having different phase for the two measuring detectors, said signal processing means comprising means for combining the signals from the two measuring detectors to provide a resulting phase difference signal, and means being provided for separating resulting phase difference signals caused by a phase difference between the doppler signals for the two measuring detectors exceeding $2\pi$.

In the following, the invention will be further explained with reference to the schematical drawings, in which FIG. 1 is a principle diagram of a usual laser-doppler apparatus of the kind used for measurement of flow velocity of a fluid flow;

Figure 1:
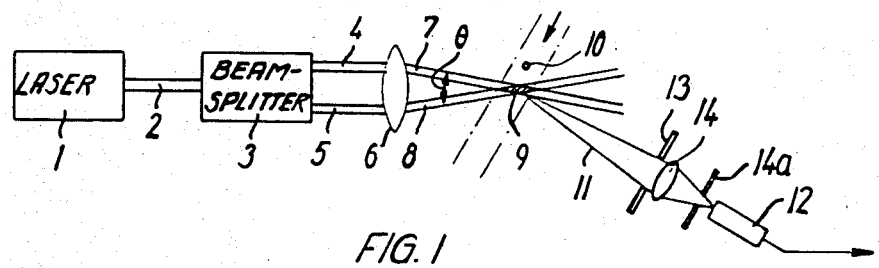

FIG. 1 shows the optical parts of a laser-doppler-arrangement of the kind used in a usual laser-doppler-anemometer for measuring the flow velocity of a fluid. A beam of radiation 2 from a laser 1 is separated in a beam splitter 3 into two parallel beams of radiation 4 and 5, which may have the same wave length, i.e. frequency, or be displaced in frequency in a manner known per se by means, for instance, of a Bragg-cell in the path of one beam.

By passing through a focusing optics 6, which is shown in the figure as a single lense, the beams of radiation 4 and 5 will be deflected into two converging beams of radiation 7 and 8, which are focused, i.e. intersect each other, in a limited spatial region 9 constituting the measuring volume of the apparatus. In the practical use of the apparatus, the arrangement is designed and positioned so that the measuring volume 9 will be located in a fluid flow including moving particles, of which only one is shown at 10, so that a part of this flow is caused to pass the measuring volume 9.

In the measuring volume 9, the incoming laser beams 7 and 8 intersecting each other will give rise to scattered radiation from a particle moving through the measuring volume 9, and in a usual anemometer arrangement, the scattered radiation in a given reflection direction 11 is detected by means of a photodetector 12 with an associated aperture 13 and detector optics including a lense 14 and a viewing field limiting member 14a, such as a pin hole. The photodetector 12 is connected to the electrical signal processing means of the apparatus.

The measuring principle with an apparatus as shown in FIG. 1 is based on measurement of the difference between the doppler frequency shifts in the scattered rays from the moving particle caused by the two incoming laser beams 7 and 8. By causing these two scattered radiation beams to impinge simultaneously onto a photodetector, the difference frequency between the two doppler-displaced frequencies for the scattered radiation beams is formed, and this difference frequency is directly proportional to the velocity component of the moving particle at right angles to the bisector between the two incoming beams 7 and 8 and positioned in the plane of these radiation beams, i.e. the plane of the paper in FIG. 1.

As further elaborated in the following, the present invention is based on the recognition of the fact that the doppler signal thus detected in addition to the information about the velocity of a moving particle given by the frequency of the signal also contains information about the size of the particle.

Since a photodetector in an arrangement as shown in FIG. 1 may be constituted by a photo multiplier having a square characteristic, the resulting photo current constituting the output signal of the detector may be expressed by $$i(t) = \int_A |E_1(t) + E_2(t)| \, d^2A \quad (1)$$

where $E_1(t)$ and $E_2(t)$ are the optical fields for the beams of scattered radiation from a moving particle caused by one and the other of the two incoming laser beams 7 and 8 in FIG. 1. This photo current will comprise a d.c.-part and an a.c.-part, of which the a.c.-part comprises the difference frequency between the frequencies $f_1$ and $f_2$ of the beam fields impinging on the detector, i.e.

$$i(t) \approx |E_1|^2 + |E_2|^2 + 2|E_1||E_2| \cos(2\pi(f_2-f_1)t) \quad (2)$$

Figure 2:
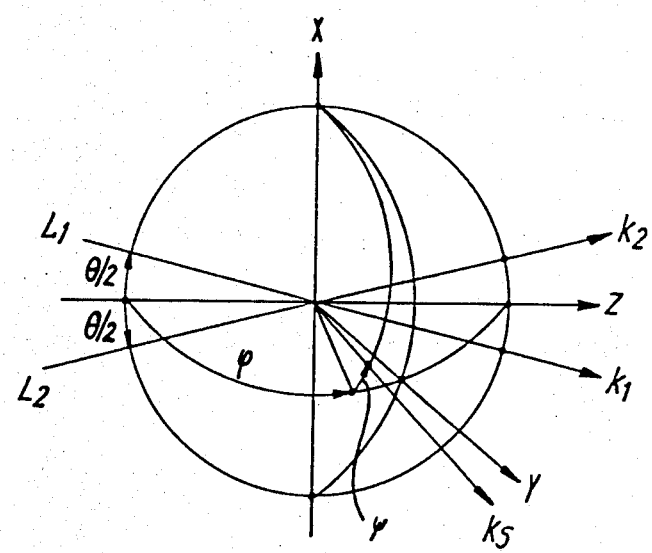
FIG. 2 is a spatial coordinate system with vectors for the focused laser beams impinging into the measuring volume in the apparatus design of FIG. 1, as well as the scattered radiation in the measuring direction against a detector device.

In a vector diagram as shown in FIG. 2, in which $\bar{k}_1$ and $\bar{k}_2$ indicate the wave vectors for the two incoming laser beams 7 and 8, and $\theta$ is the angle between these beams, the doppler frequency $f_D$ may be expressed by $$f_D = f_2 - f_1 = m\bar{u} \cdot (\bar{k}_2 - \bar{k}_1) \quad (3)$$

$$= (2n \cdot u_x/\lambda) \cdot \sin(\theta/2)$$

where $\bar{u}$ is the velocity vector for the moving particle, $\lambda$ the wave length of the laser radiation, and $u_x$ the component of the velocity vector u at right angles to the bisector between the laser beams 7 and 8, i.e. in the x-direction in the spatial coordinate system in FIG. 2.

In a simplified way of expression, the doppler frequency $f_D$ may be considered a result of the passage of the moving particle through a set of parallel interference planes positioned in the measuring volume defined by the crossing region between the laser beams 7 and 8 and consisting of alternate regions of light and dark.

However, this way of description is valid only for a particle so small that it can be considered punctiform relative to the separation of the interference planes. If the size of the particle approaches the separation of the interference planes, interference effects will appear in the combination of scattered radiation from different areas of the particle, which will cause a phase displacement of the doppler signal.

As an example of this, an important particular situation is described in the following, where the scattered radiation from a moving spherical particle is considered emanating from two points on the surface of the particle. The example is descriptive for the physical relations in measurement on spherical particles in the form of droplets in air or bubbles in liquids, but may be extended in a simple way to more complicated particle shapes, if only the scattering relations are known.

In the coordinate system in FIG. 2, $L_1$ and $L_2$ indicate the axes in the X-Z-plane for the incoming laser beams corresponding to the beams 7 and 8 in FIG. 1, which beams may be described by wave vectors $\bar{k}_1$ and $\bar{k}_2$ forming angles $+\theta/2$ and $-\theta/2$ with the Z-axis. The scattered radiation against a detector is indicated by the wave vector $\bar{k}_s$, the direction of which is defined by the angle $\phi$ in the Y-Z-plane and the angle $\psi$ from the Y-Z-plane to the vector $\bar{k}_s$. In the above mentioned particular situation of measurement on bubbles in liquid, the angle $\phi$ may advantageously be chosen to about 98°, since the reflection from a bubble surface in these directions are dominating relative to the scattered radiation passing through the bubble.

By reflection of the surface of a spherical particle which is considered to have its center in the center of the coordinate system shown in FIG. 2, each of the beams $L_1$ and $L_2$ will cause a scattered beam in the direction of the vector $\bar{k}_s$.

For the incident beams having directions corresponding to the vectors $\bar{k}_1$ and $\bar{k}_2$, the angles of incidence $i_1$ and $i_2$ of the reflection points, not shown in FIG. 2, which cause scattered rays with a direction corresponding to the vector $\bar{k}_s$, i.e. the angle between the incident ray in question and the radius vector in the scpherical coordinate system to the point of reflection may be expressed by $$\cos i_1 = \frac{\bar{k}_s \cdot (\bar{k}_s - \bar{k}_1)}{(\bar{k}_s)(\bar{k}_s - \bar{k}_1)} \tag{4}$$

$$\cos i_2 = \frac{\bar{k}_s \cdot (\bar{k}_s - \bar{k}_2)}{(\bar{k}_s)(\bar{k}_s - \bar{k}_1)} \tag{5}$$

where the vectors $\bar{k}_1$, $\bar{k}_2$ and $\bar{k}_s$ in the illustrated coordinate system will have the coordinates $\bar{k}_1 = k(-\sin \theta/2, 0, \cos \theta/2)$ $\bar{k}_2 = k(\sin \theta/2, 0, \cos \theta/2)$ $\bar{k}_s = k(\sin \psi, \cos \psi \sin \phi, -\cos \psi \cos \phi)$ whereby the following expressions will apply for the angles $i_1$ and $i_2$ $$\cos i_1 = \frac{1}{\sqrt{2}} \sqrt{1 + \sin \frac{\theta}{2} \sin \psi + \cos \frac{\theta}{2} \cos \psi \cos \phi} \tag{6}$$

$$\cos i_2 = \frac{1}{\sqrt{2}} \sqrt{1 - \sin \frac{\theta}{2} \sin \psi + \cos \frac{\theta}{2} \cos \psi \cos \phi} \tag{7}$$

For the scattered rays having a direction corresponding to the vector $\bar{k}_s$ caused by each of the incident rays having directions corresponding to the vectors $\bar{k}_1$ and $\bar{k}_2$, respectively, the phases will then be $$\Phi_1 = n\bar{u}t \cdot (\bar{k}_s - \bar{k}_1) + 2kRn \cdot \cos i_1 + \Phi_o \tag{8}$$

$$\Phi_2 = n\bar{u}t \cdot (\bar{k}_s - \bar{k}_2) + 2kRn \cdot \cos i_2 + \Phi \tag{9}$$

where $\Phi_o$ is the phase for a scattered ray caused by an incident ray in a plane through the center of the moving particle, i.e. the X-Z-plane in FIG. 2.

By detection with a detector arranged in the remote field in the direction of the vector $\bar{k}_s$, the doppler frequency is obtained as the difference frequency between the two scattered rays caused by incident rays having directions corresponding to the vectors $\bar{k}_1$ and $\bar{k}_2$. This doppler signal will have the phase $$\Phi = \Phi_2 - \Phi_1 = n\bar{u}t(\bar{k}_1 - \bar{k}_2) + 2n \cdot kR(\cos i_2 - \cos i_1) \tag{10}$$

Figure 3:
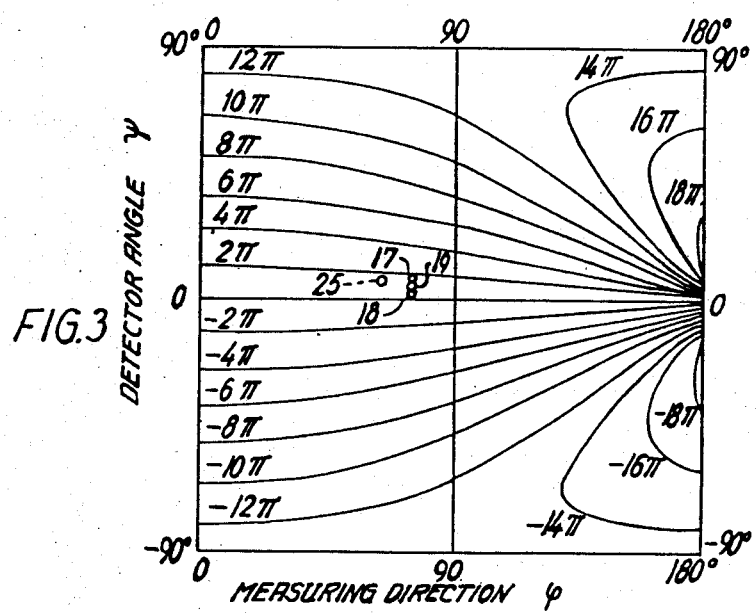
FIG. 3 is a phase diagram for the scattered radiation.

For the above mentioned particular situation, FIG. 3 shows a phase diagram for the phase $\Phi$ as a function of the adjustment angles $\phi$ and $\psi$ for a detector. The curves in the diagram form equiphase lines for determination of the values of $\phi$ and $\psi$ in spatial positions, in which the doppler signal will have the same phase.

Figure 4:
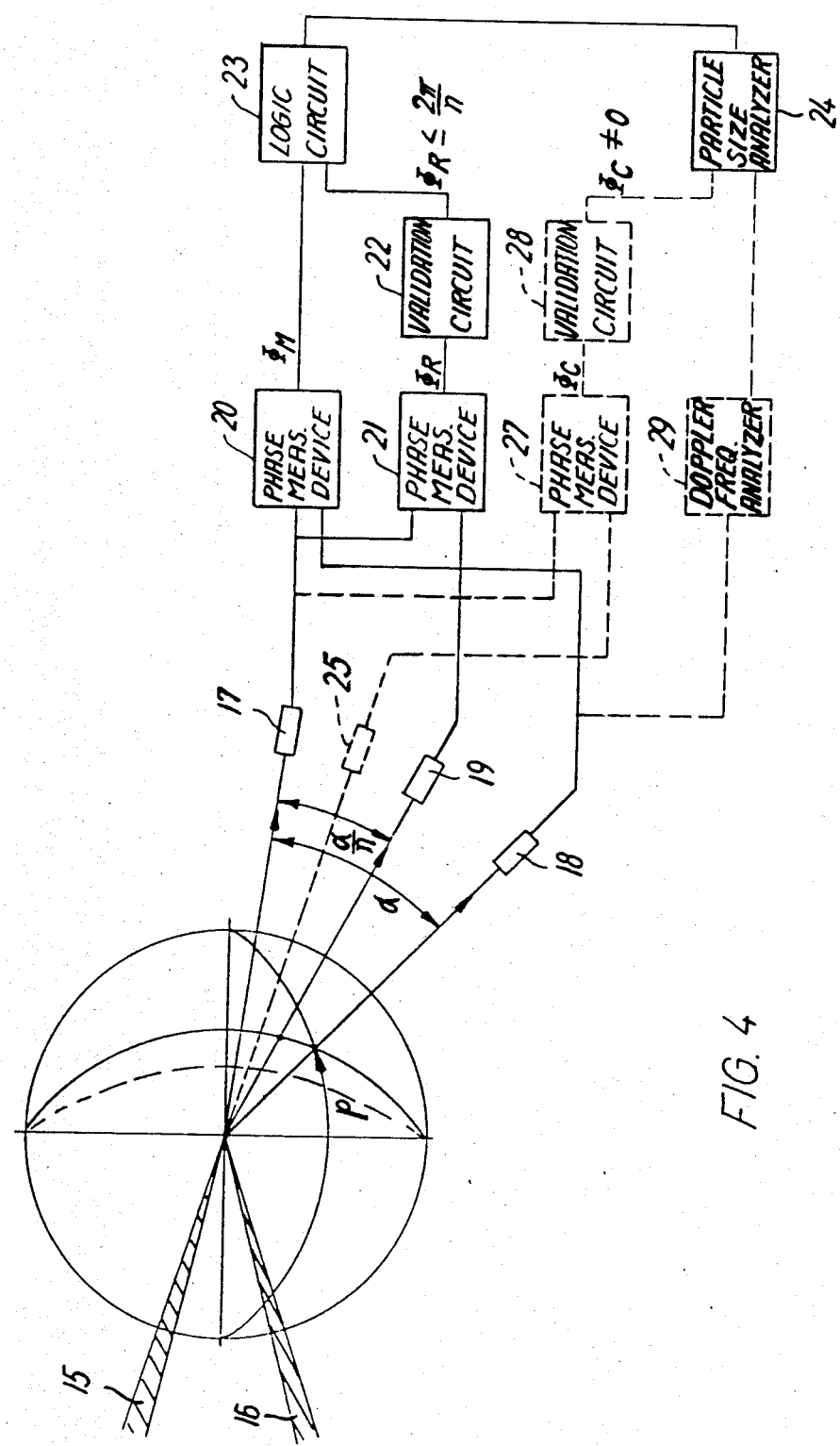
FIG. 4 is a principle diagram corresponding to that of FIG. 2 for illustrating a possible location of detector means as well as the construction of signal processing circuits in a laser-doppler-apparatus according to the invention.

If, as shown in FIG. 4, the measuring detectors 17 and 18 and the reference detector 19 are positioned so that the beam directions to these detectors lie in a detecting plane comprising the line through the crossing point of the beams perpendicular to the bisector of the incoming laser beams 15 and 16, i.e. the X-axis in the coordinate system in FIG. 2, it will appear from the phase diagram in FIG. 3 that the condition for an unambiguous resulting phase difference signal from the measuring detectors 17 and 18 corresponding to an unambiguous determination of a particle size below the prescribed maximum particle size corresponding to the position of the measuring detectors will be that the phase reference signal $\Phi_R$ is smaller than or equal to $2\pi/n$ where n is the ratio of the angular separation $\alpha$ between the beam directions to the measuring detectors 17 and 18 to the angular separation $\alpha/n$ between the beam directions to the reference detector 19 and the measuring detector cooperating therewith.

In order to realize the above mentioned unambiguity, i.e. to separate phase difference signals from the measuring detectors 17 and 18, which are expressions of a phase difference above $2\pi$, the signal processing means according to the invention may, as shown in FIG. 4, comprise a first phase measuring device 20 which is connected to the two measuring detectors 17 and 18 for determining the phase difference between the doppler signals received by these detectors and a second phase measuring device 21 connected to the reference detector 19 and the one measuring detector 17 for determining the phase difference between the doppler signals received by these detectors. The output of the second phase measuring device 21 may be connected to a validation circuit 22 for determining whether the phase reference signal $\Phi_R$ fulfils the above mentioned condition.

To the validation circuit 22 and the first phase measuring device 20, a logic circuit is connected, which only in response to an actuation signal from the validation circuit 22 when the above mentioned condition is complied with, transfer the resulting phase difference signal $\Phi_M$ from the first phase measuring device 20 to a particle size analyzer 24 which may be designed to calculate and record for a fluid flow under examination the distribution of particle sizes below the prescribed maximum size corresponding to the given adjustment of the measuring detectors as well as the absolute concentration, for instance quantity per time unit, of particles below this maximum size.

By means of the phase measuring devices 20 and 21 and the validation circuit 22 connected thereto as well as the logic circuit 23 in the diagram in FIG. 4, any resulting phase difference signal $\Phi_M$, for which it has been determined in the validation circuit 22 by means of the phase reference signal $\Phi_R$ that it has been caused by a phase difference exceeding $2\pi$ between the doppler signals for the measuring detectors 17 and 18 will be separated out, no matter the reason for its appearance. As already mentioned, the reason for detection of a phase difference exceeding $2\pi$ may, above all, be scattered radiation from a particle exceeding the prescribed maximum particle size corresponding to the actual adjustment of the angular separation $\alpha$ between the measuring detectors 17 and 18. However, a phase difference exceeding $2\pi$ may also be caused by scattered radiation from a particle having a shape deviating essentially from the spherical form. In practice, this situation will occur if in a gas or liquid flow axamined for spherical particles in the form of droplets and bubbles, respectively, also solid particles of varying shapes are present.

According to a special feature of the invention, in order to discriminate between the two above mentioned reasons for a phase difference exceeding $2\pi$ between the doppler signals to the measuring detectors 17 and 18 for the purpose of obtaining information about the presence of solid particles in the fluid flow under examination, a further reference detector 25 may be used, which is adjusted to such a spatial position that it will receive for a spherical particle a doppler signal having the same phase as one of the measuring detectors, for example the measuring detector 17. In the phase diagram in FIG. 3, this corresponds to a location of the doppler signal for the detector 25 on the same equiphase line as the doppler signal for the detector 17.

The signal from the detector 25 is now supplied together with the signal from the measuring detector 17 to the third phase measuring devide 27 to produce a phase comparison signal $\Phi_C$. This phase comparison signal is supplied to a validation circuit 28, which separates phase comparison signals $\Phi_C$ having the resulting phase 0, i.e. caused by detection of spherical particles. The output signals from the validation circuit 28 complying in this way with the condition $\Phi_C = 0$ corresponding to detection of a particle of a non-spherical shape is supplied to the particle size analyzer 24 for information about the content of such solid particles in the fluid flow under examination.

In order to perform a quantitative particle analysis in the analizer 24, information about the velocity of the fluid flow under examination is required in addition to the collection of data about particle sizes and size distributions. Such a velocity information may be obtained in a known manner in that a doppler frequency analyzer 29, from which velocity information is supplied to the particle size analyzer 24, is connected to one of the detectors, for example the measuring detector 18.

Figure 5:
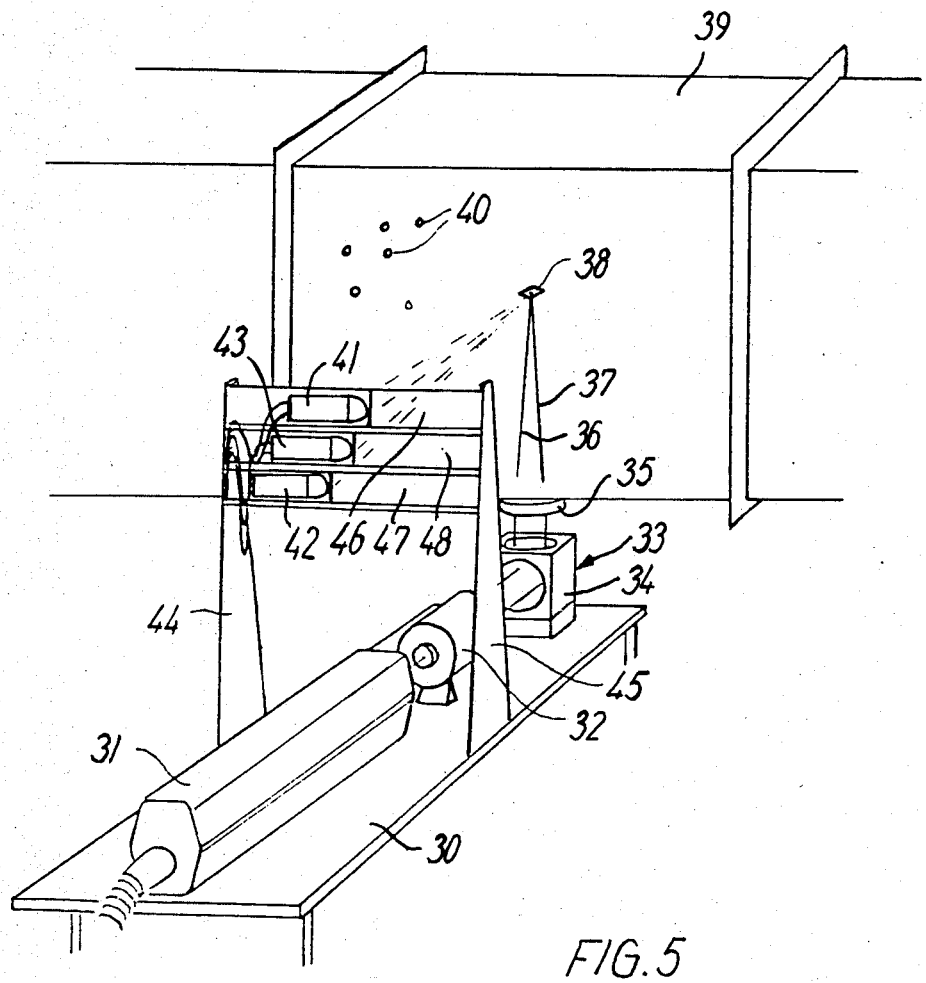
FIG. 5 is a possible practical embodiment for the setting-up of laser optics and detector means in a laser-doppler-apparatus according to the invention.

In FIG. 5, a possible practical embodiment of the optical parts of a laser-doppler-apparatus according to the invention is shown.

On a stable optical bench 30, there is arranged a laser 31, a beam splitter 32 and a focusing unit 33 having a focusing front lense 35, by means of which laser beams 36 and 37 are caused to intersect with each other in a measuring volume 38 in a pipe line 39 passed by the fluid flow to be examined, and the moving particles 40 carried thereby. For controlling the angle of intersection $\theta$ between the focused laser beams 36 and 37 and thereby adjusting the measuring volume and the actual variation range for particle sizes, adjusting members may be associated with the beam splitter 32 in a manner known per se for controlling the separation of the parallel partial beams leaving the beam splitter.

A holder for two measuring detectors 41 and 42 and a reference detector 43 comprises two posts 44 and 45 displaceable on the optical bench 30, and mounting plates 46, 47 and 48 for the detectors 41, 42 and 43, respectively, said mounting plates being connected with the posts 44 and 45 in such a way as to be individually displaceable in the direction at right angles to the optical bench 30, i.e. parallel to the by-sector of the laser beams 36 and 37.

In each of the mounting plates 46, 47 and 48, the actual detector is, moreover, arranged so as to be displaceable in the transverse direction at right angles to posts 44 and 45, i.e. at right angles to the by-sector of the beams 36 and 37.

The basic arrangement of the detectors 41 to 43, shown in FIG. 5, corresponds in the diagram of FIG. 4 to an arrangement of the detectors in a plane normal to the focusing plane comprising the beams 36 and 37 and intersecting the latter plane in the bisector of the beams, i.e. corresponding to the Y-Z-plane in FIG. 2. The adjustment may now be performed in such a way that with the reference detector 43 maintained in the basic position on the mounting plate 48, the measuring detector 41 is displaced to one side relative to the basic position, and the measuring detector 42 to the other side relative to the basic position.

In the diagram in FIG. 4, this adjustment will correspond to a turning of the detecting plane from the above mentioned basic position, the Y-Z-plane in FIG. 2, to an oblique position, in which the detecting plane has been turned an angle around the beam direction to the reference detector 43 relative to the basic position. With the embodiment shown, this turning angle may, for instance, be up to 45°, but even if the detecting plane does not thereby attain the position shown in FIG. 4, which has been used as basis for explanation of the signal processing, this does not change anything in the detecting principle, since the three detectors 41 to 43 are still adjusted to spatial positions, in which they receive doppler signals within one and the same phase band in the phase diagram in FIG. 3 for a prescribed maximum particle size.

The adjustment to a desired particle size variation range may be performed by a combination of longitudinal displacement of the detector holder with the posts 44 and 45 on the optical bench 30, mutual displacement of the detector mounting plates 46 to 48 relative to the posts 44 and 45 and the above mentioned displacement of the measuring detectors 41 and 42 on the mounting plates 46 and 47 for turning the detecting plane.

As it will appear from the foregoing, adjustment to a small maximum particle size is made by performing the adjustment in such a way that the angular separation of the directions of detecting rays to the measuring detectors 41 and 42 is increased, i.e. by approaching the posts 44 and 45 to the focusing unit 33, increasing the mutual separation of the mounting plates 46 to 48 and increasing the displacement of the detectors 41 and 42 on the mounting plates 46 and 47 relative to the basic position shown.

Conversely, adjustment to a greater maximum particle size is performed in such a way that the angular separation of the directions of detecting rays to the measuring detectors 41 and 42 is reduced, i.e. by removing the detector holders with the posts 44 and 45 from the focusing unit 33, reducing the mutual separation of the mounting plates 46 to 48 and/or reducing the displacement of the detectors 41 and 42 on the mounting plates 46 and 47.

In this way it is possible to perform adjustment of the apparatus to a very great variation range of particle sizes, for instance for detecting particles quite down to an order corresponding to the wave length of the laser radiation up to a particle diameter several thousand times bigger.

Corresponding to the diagram in FIG. 4, the apparatus embodiment shown in FIG. 5 may be supplied with a further reference detector for use in the detection of solid particles, and the signal processing circuit of the apparatus, which is not illustrated and to which the detectors are connected through a cable 49, may be embodied as explained with reference to FIG. 4.

We claim:

1. A laser-doppler-apparatus for determining the size of moving spherical particles in a fluid flow, comprising a laser beam generator for generating two spatially separated laser beams, focusing means for focusing the laser beams to produce focused beams in a focusing plane which intersect each other under a given angle in an intersecting point in a measuring volume passed by a part of the fluid flow, photoelectric detector means for detecting the scattered radiation caused by a moving particle in the fluid flow in spatially different positions outside the measuring volume and generating electrical signals in response thereto, and signal processing means for determining the particle size on the basis of said electrical signals, characterized in that the detector means comprise two measuring detectors and means for adjusting the detectors into spatial positions, for which in a detecting plane, the beam directions from said intersecting point to the measuring detectors have an angular separation corresponding to a predetermined maximum particle size, for receiving scattered beams from the moving particle in the form of doppler signals having different phase for the two measuring detectors, said signal processing means comprising means for combining the signals from the two measuring detectors to provide a resulting phase difference signal, and means being provided for separating resulting phase difference signals caused by a phase difference between the doppler signals for the two measuring detectors and exceeding $2\pi$.

2. A laser-doppler-apparatus as claimed in claim 1, characterized in that said separating means comprises a reference detector, for which the beam direction from said intersecting point extends in the detecting plane between the beam directions to the two measuring detectors, said signal processing means comprising means for combining the signal from the reference detector and the signal from one measuring detector for providing a phase reference signal to indicate whether a resulting phase difference signal is caused by a phase difference between the doppler signals from the two measuring detectors exceeding $2\pi$.

3. A laser-doppler-apparatus as claimed in claim 2, characterized in that the combination means in said signal processsng means comprise a first phase measuring device connected to the two measuring detectors, a second phase measuring device connected to the reference detector and one of the measuring detectors, a validation circuit connected to the other phase measuring device and a logic circuit connected to the validation circuit and said first phase measuring device for transferring a resulting phase difference signal from the first phase measuring device to a particle size analyzer in response to an actuation signal from the validation circuit, said validation circuit being adapted to supply said actuation signal only when the phase difference signal from the second phase measuring device is smaller than or equal to $2\pi/n$, where n is the ratio between (i) the angular separation in the detecting plane between the beam directions to the measuring detectors and (ii) the angular separation in the detecting plane between the beam directions to the reference detector and said one measuring detector, respectively.

4. A laser-doppler-apparatus as claimed in claim 2, characterized in that said detector means comprise a further reference detector and means for adjusting said detector into a spatial position, where the beam direction to it from said intersecting point extends outside the detecting plane for the beam directions to the other detectors and in such a position relative to the beam direction to one of the other detectors that in response to scattered radiation from a spherical particle, it will receive a doppler signal having the same phase as for one said one detector, said signal processing means comprising means for combining the signals from said further reference detector and said one measuring detector to provide a phase comparison signal and supplying an output signal when in response to detection of a non-spherical particle said phase comparison signal is of a value deviating from zero.

5. A laser-doppler-apparatus as claimed in claim 4, characterized in that said combining means comprise a further phase measuring device connected to said further reference detector and said one measuring detector and a validation circuit connected with said phase measuring device for transferring said output signal to said particle size analyzer in response to said value deviating from zero of said phase comparison signal.

6. A laser-doppler-apparatus as claimed in claim 1 characterized in that a doppler frequency analyzer is connected to one of said detectors to supply a velocity information signal.

7. A laser-doppler-apparatus as claimed in claim 1 characterized in that adjusting means for said detectors are arranged to adjust the detectors to spatial positions within a variation range down to a particle size of the same order as the wave length of the laser radiation, means being associated with the laser beam generator to adjust the intersection angle between the laser beams focused in the measuring volume.

* * * * *

UNITED STATES PATENT AND TRADEMARK OFFICE
CERTIFICATE OF CORRECTION

PATENT NO. : 4,701,051
DATED : October 20, 1987
INVENTOR(S) : Buchhave et al

It is certified that error appears in the above-identified patent and that said Letters Patent are hereby corrected as shown below:

Title page, item [73] should read as follows:

-- [73] Assignee: DANTEC ELEKTRONIK, MEDICINSK OG VIDENSKABELIGT MÅLEUDSTYR A/S, Skovlunde, Denmark --

Signed and Sealed this

Sixteenth Day of August, 1988

Attest:

DONALD J. QUIGG

*Attesting Officer*

Commissioner of Patents and Trademarks